(12) United States Patent
Sheng et al.

(10) Patent No.: US 10,675,276 B2
(45) Date of Patent: Jun. 9, 2020

(54) DOSING PREPARATION OF DABIGATRAN ETEXILATE OR A SALT THEREOF AND A PREPARATION METHOD THEREOF

(71) Applicant: Hangzhou SoliPharma Co., Ltd., Hangzhou, Zhejiang (CN)

(72) Inventors: Xiaoxia Sheng, Hangzhou (CN); Yong Tang, Hangzhou (CN)

(73) Assignee: HANGZHOU SOLIPHARMA CO., LTD., Hangzhou (CN)

( * ) Notice: Subject to any disclaimer, the term of this patent is extended or adjusted under 35 U.S.C. 154(b) by 272 days.

(21) Appl. No.: 15/308,014

(22) PCT Filed: Oct. 8, 2015

(86) PCT No.: PCT/CN2015/091437
§ 371 (c)(1),
(2) Date: Oct. 31, 2016

(87) PCT Pub. No.: WO2016/070696
PCT Pub. Date: May 12, 2016

(65) Prior Publication Data
US 2017/0049764 A1    Feb. 23, 2017

(30) Foreign Application Priority Data
Nov. 3, 2014   (CN) .......................... 2014 1 0610015

(51) Int. Cl.
| A61K 31/4439 | (2006.01) |
| A61K 9/00 | (2006.01) |
| A61K 9/50 | (2006.01) |
| A61K 9/48 | (2006.01) |

(52) U.S. Cl.
CPC ........ *A61K 31/4439* (2013.01); *A61K 9/0053* (2013.01); *A61K 9/4866* (2013.01); *A61K 9/5015* (2013.01); *A61K 9/5047* (2013.01); *A61K 9/5078* (2013.01); *A61K 9/5089* (2013.01)

(58) Field of Classification Search
None
See application file for complete search history.

(56) References Cited

U.S. PATENT DOCUMENTS

| 5,395,626 A | * | 3/1995 | Kotwal | ............... A61K 9/5078 424/456 |
| 2004/0043073 A1 | * | 3/2004 | Chen | ................... A61K 9/2009 424/486 |

(Continued)

FOREIGN PATENT DOCUMENTS

| AU | 742593 B3 | 1/2002 | | |
| CN | 1638771 A | * | 7/2005 | ......... A61K 31/4439 |

(Continued)

OTHER PUBLICATIONS

English Language Translation of CN 103127109 A. (Year: 2013).*

(Continued)

*Primary Examiner* — Dominic Lazaro
(74) *Attorney, Agent, or Firm* — Sterne, Kessler, Goldstein & Fox P.L.L.C.

(57) ABSTRACT

The present invention relates to two novel oral pharmaceutical compositions of dabigatran etexilate or its pharmaceutically acceptable salts thereof, and the processes of preparation thereof.

16 Claims, 3 Drawing Sheets

(56) References Cited

U.S. PATENT DOCUMENTS

| | | | |
|---|---|---|---|
| 2005/0118264 A1* | 6/2005 | Sela | A61K 9/5026 424/469 |
| 2006/0183779 A1* | 8/2006 | Brauns | A61K 31/4439 514/338 |
| 2010/0255090 A1* | 10/2010 | Rubino | A61K 9/1611 424/465 |

FOREIGN PATENT DOCUMENTS

| | | | |
|---|---|---|---|
| CN | 1638771 A | | 7/2005 |
| CN | 103127109 A | * | 6/2013 |
| CN | 103127109 A | | 6/2013 |
| WO | WO 98/37075 | | 8/1998 |
| WO | WO 03/074056 A1 | | 9/2003 |
| WO | WO-2013124340 A1 | * | 8/2013 |

OTHER PUBLICATIONS

English language translation of CN 1638771 A (Year: 2005).*
International Search Report and Written Opinion for International Application No. PCT/CN2015/091437, State Intellectual Property office of the P.R. China, China, dated Jan. 11, 2016, 5 pages.

* cited by examiner

DOSING PREPARATION OF DABIGATRAN ETEXILATE OR A SALT THEREOF AND A PREPARATION METHOD THEREOF

FIELD OF THE INVENTION

The present invention relates to the technical field of pharmaceutical technology. Specifically, the present invention relates to the novel, orally administered forms of 3-[(2-{[4-(hexyloxycarbonylamino-imino-methyl)-pheny-lamino]-methyl}-1-methyl-1H-benzimidazol-5-carbonyl)-pyridin-2-yl-amino] propionic acid ethyl ester, generic name dabigatran etexilate, or pharmaceutically acceptable salts thereof and their preparation processes. Specifically, the present invention relates to two oral pharmaceutical compositions and their preparation processes for dabigatran etexilate and the pharmaceutically acceptable salts thereof.

BACKGROUND

Dabigatran etexilate, a novel direct thrombin inhibitor, is a prodrug of dabigatran and is a non-peptide thrombin inhibitor. It was developed by Boehringer Ingelheim Pharmaceuticals, Inc. The oral drug is absorbed by the gastrointestinal tract and converts to dabigatran which has the direct anticoagulant activity. Dabigatran binds to the specific fibrin-binding sites of thrombin, preventing cleavage of fibrinogen to fibrin and blocking the final steps in the coagulation cascade network and thrombosis. Dabigatran can be dissociated from a fibrin-thrombin complex and play reversible anticoagulant effect. Dabigatran etexilate was first approved in Germany and England in April 2008. It was approved by the U.S. Food and Drug Administration (FDA) in October 2010 for reducing the risks of stroke or systemic embolism in patients with non-valvular atrial fibrillation. Currently, the approved dosage form is capsules with strengths of 75 mg and 150 mg, and the product name is Pradaxa®.

The chemical name of dabigatran etexilate is 3-[(2-{[4-(hexyloxycarbonylamino-imino-methyl)-pheny-lamino]-methyl}-1-methyl-1H-benzimidazol-5-carbonyl)-pyridin-2-yl-amino] propionic acid ethyl ester, having a formula of C34H41N7O5, a molecular weight of 627.74 and a chemical structural formula shown below (I):

Patent document WO98/37075 discloses the compound of dabigatran and its uses. Patent documents CN1638771A and WO03/074056A1 disclose a composition of dabigatran, and the composition contains the following main components: a core material consisting of an organic acid, an insulating layer and an active substance layer.

The patent document CN103127109A discloses a dabigatran etexilate composition containing the following main components: a core material containing the active substance, an insulating layer and an organic acid layer.

The present inventors discovered that in the composition prepared according to WO03/074056A1, since the active drug substance is in the outer layer of the pellet, the active drug is more prone to phase transformation and degradation. The present inventors also discovered that the composition prepared according to the patent document CN103127109A has a similar dissolution rate to that of a reference preparation (prepared according to CN1638771A) in the acid dissolution medium. However, in water, their dissolution rates are too different to be considered as to be similar in terms of in vitro dissolution.

In view of the problems in the prior arts, it is very important to develop a novel orally administered form of dabigatran etexilate or its pharmaceutical acceptable salts with more advantageous features.

SUMMARY OF THE INVENTION

The object of the present invention is to provide an improved, orally administered formulation of dabigatran etexilate and the pharmaceutically acceptable salts thereof.

According to the object of the present invention, the present invention provides an orally administered pharmaceutical composition 1 (herein referred to as "Composition 1") of dabigatran etexilate or its pharmaceutical acceptable salts and preparation processes thereof.

The orally administered pharmaceutical Composition 1 of dabigatran etexilate or pharmaceutical acceptable salts thereof includes:

a) one or more approximately spherically-shaped pellet cores consisting of a binder and pharmaceutically acceptable celluloses or sugars or starches, or consisting of one or more component(s) selected from microcrystalline cellulose or sugars or starches, b) a first active substance layer consisting of the active substance, and/or a disintegrant, and/or a filler, and a binder, in which the active substance is dabigatran etexilate or one pharmaceutically acceptable salt thereof;

c) a first water soluble isolating layer surrounding the active substance layer and the layer material is selected from the group consisting of hydroxypropyl methyl cellulose, hydroxypropyl cellulose, starch, resin and other organic polymers or combinations of these organic materials;

d) an acid layer comprising a binder and a pharmaceutically acceptable organic acid or comprises an organic acid. The organic acid has a solubility in water of more than 1 g/250 ml at 20° C. and is selected from the group consisting of tartaric acid, fumaric acid, succinic acid, citric acid, malic acid, glutamic acid or aspartic acid or a hydrate or salt of glutamic acid or aspartic acid, and hemi-cysteine hydrochloride;

e) a second water soluble isolating layer surrounding the acid layer, and the layer material is selected from the group consisting of hydroxypropyl methyl cellulose, hydroxypropyl cellulose, starch, resin and other water soluble polymers or combinations of these polymers;

f) a second active substance layer consisting of the active substance, and/or a disintegrant, and/or a filler and a binder, in which the active substance is dabigatran etexilate or one pharmaceutically acceptable salt thereof; and g) a third soluble isolating layer surrounding the active substance layer and the layer material is selected from the group consisting of hydroxypropyl methyl cellulose, hydroxypropyl cellulose, starch, resin and other organic polymer material or combinations of these organic materials.

Preferably, the fillers are pharmaceutically acceptable water soluble materials; more preferably, one or more component(s) selected from sugars, alcohols, soluble starches and salts; even more preferably, lactose, mannitol, maltose and sorbitol.

Preferably, the mass ratio of the filler to the active substance is 1:1 to 1:10 and more preferably 1:2 to 1:5.

Preferably, the component of the pellet core is sugar, more preferably sucrose.

Preferably, the amount of the pallet core is 10 to 60%.

Preferably, the organic acid is cysteine hydrochloride.

Preferably, the amount of the organic acid is 15 to 60%.

Preferably, the content of dabigatran etexilate or its pharmaceutical acceptable salt is 15 to 60%.

Preferably, the binder is selected from the group consisting of hydroxypropyl methyl cellulose, hydroxypropyl cellulose, methyl cellulose, hydroxyethyl cellulose, carboxymethyl cellulose, polyethylene pyrrolidone, N-vinyl pyrrolidone and copolymers of vinyl acetate or combinations of these copolymers, more preferably hydroxypropyl cellulose.

Preferably, the average particle size of the pellet core is 0.2 to 1.5 mm.

Preferably, the amount of the binder in the active substance layer is 0.5 to 20%, more preferably 2 to 10%.

Preferably, the amount of the binder in the organic acid layer is 0.5 to 20%, more preferably 2 to 10%.

Preferably, the amount of the first isolating layer surrounding the active substance layer is 2.0 to 10%, the amount of the second isolating layer surrounding the organic acid layer is 2.0 to 10%.

Figure 1:
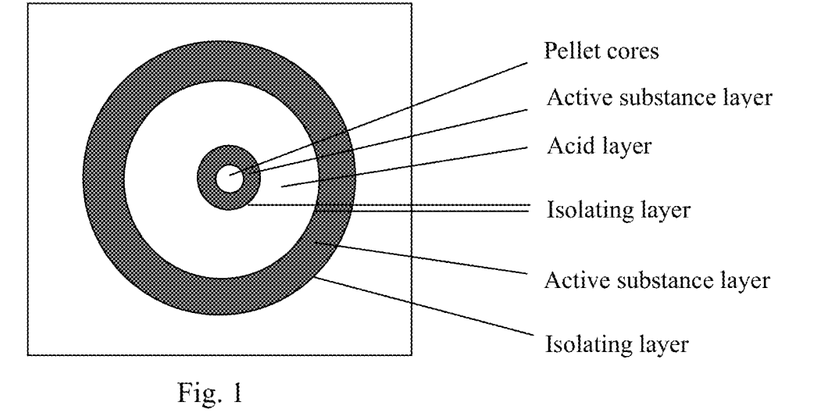
FIG. 1 is the schematic structure of the pharmaceutical Composition 1.

A preferred embodiment of the composition is a multiparticulate formulation and the structure of the particles is shown in FIG. 1.

In some embodiments, to improve the dissolution rate of the dosage form, fillers such as lactose, mannitol, maltose, and sorbitol are added into the active substance layer.

FIG. 1 illustrates the schematic structure of the pharmaceutical composition, a section view of a suitable pellet for the preparation of Composition 1. The approximately spherically-shaped core of this pellet contains sucrose. The core is surrounded by the first active substance layer which contains the binder and the active substance or contains the binder, the water soluble filler and the active substance. The layer surrounding the first active substance layer is the first water soluble isolating layer which separates the active substance layer and the organic acid layer. This isolating layer is surrounded by the likewise spherically-shaped organic acid layer containing the binder and the organic acid. Over this acid layer is the second water soluble isolating layer, which separates the active substance layer and the organic acid layer. Over the second water soluble isolating layer is the second active substance layer containing the binder and the active substance or containing the binder, the water soluble filler and the active substance. The outermost layer is the third isolating layer containing organic polymer materials. This isolating layer serves to increase the abrasion resistance and the shelf life of the pellets.

The preparation method of the Composition 1 is as follows:

(1) coating an pellet core with the first active substance layer consisting of the binder and the active substance or containing the binder, the filler and the active substance and drying;

(2) coating the first active substance layer with the first isolating layer containing polymer materials and drying;

(3) coating the first isolating layer with an organic acid layer containing the binder and the pharmaceutically acceptable organic acid by the stacking method and drying;

(4) coating the organic acid layer with the second isolating layer and drying;

(5) coating the second isolating layer with the second active substance layer containing the binder and the active substance or containing the binder, the filler and the active substance and drying;

(6) coating the second active substance layer with the third isolating layer containing polymer materials and drying;

(7) filling hard capsules with the obtained pellets containing the active substance.

The advantages of Composition 1 are as follows:

1) compared to the scheme described in the patent document WO98/37075, in Composition 1, the acid layer is sandwiched between two active substance layers and the active substance, which can better use the acid environment provided by the acids and thus can reduce the amount of the acids needed, avoiding other physiological effects to human bodies induced by excess acids;

2) compared to the scheme described in the patent document CN103127109, Composition 1 has better dissolution in many dissolution media, especially in the near neutral dissolution media such as in water, indicating a better bioavailability in people with insufficient gastric acid secretion;

3) the pellet core made by sugars is low cost and its preparation is simple.

According to the object of the present invention, the present invention provides another orally administered pharmaceutical composition 2 (herein referred to as "Composition 2") of dabigatran etexilate or pharmaceutically acceptable salts thereof and preparation processes.

The orally administered pharmaceutical Composition 2 of dabigatran etexilate or its pharmaceutically acceptable salts includes:

a) an approximately spherically-shaped acid core consisting of the acid substances, and/or a disintegrant, and/or a filler and a binder, and the acid substances are sodium dihydrogen phosphate and hemi-cysteine hydrochloride; and b) an active substance layer consisting of the active substance, and/or a disintegrant, and/or a filler and a binder, and the active substance is dabigatran etexilate or one of its pharmaceutically acceptable salt; and c) a first water soluble isolating layer between the active substance layer and the acid core, which contains the pharmaceutically acceptable hydroxypropyl methyl cellulose, hydroxypropyl cellulose, starch, resin and other organic polymer materials or combinations of these polymers; and d) a second isolating layer surrounding the active substance layer, and the layer material is selected from the group consisting of hydroxypropyl methyl cellulose, hydroxypropyl cellulose, starch, resins and other organic polymer material or combinations of these organic materials.

Preferably, the acid substance is hemi-cysteine hydrochloride.

Preferably, the content of dabigatran etexilate or pharmaceutically acceptable salts thereof is 10 to 65%.

Preferably, dabigatran etexilate or pharmaceutically acceptable salts thereof is dabigatran etexilate mesylate.

Preferably, the amount of acid substance is 8 to 65%.

Preferably, the disintegrant is selected from the group consisting of crosslinked carboxymethyl cellulose sodium, sodium carboxymethyl starch, cross-linked poly vinyl pyrrolidone, low substituted hydroxypropyl cellulose or combinations of these polymers.

Preferably, the filler is selected from celluloses, sugars, starches or combinations of these materials;

Preferably, the binder is selected from the group consisting of hydroxypropyl methyl cellulose, hydroxypropyl cellulose, methyl cellulose, hydroxyethyl cellulose, carboxymethyl cellulose, polyvinyl pyrrolidone, N-vinyl pyrrolidone and copolymers vinyl acetate or combinations of these copolymers.

Preferably, the average particle size of the acid core is 0.2 to 1.5 mm.

Preferably, the amount of the binder in the acid core is 0.5 to 20%, more preferably 2 to 10%.

Preferably, the amount of the first isolating layer between the active substance layer and the acid core is 2.0 to 10%, the amount of the second isolating layer outside of the active substance layer is 2.0 to 10%.

Figure 2:
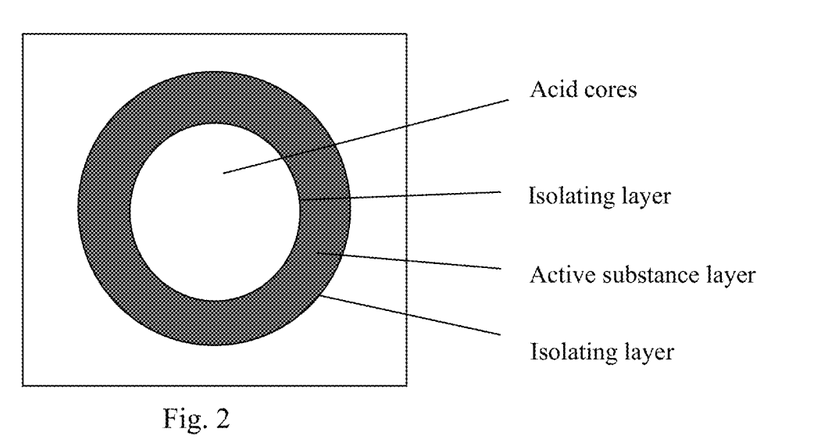
FIG. 2 is the schematic structure of the pharmaceutical Composition 2.
Figure 3:
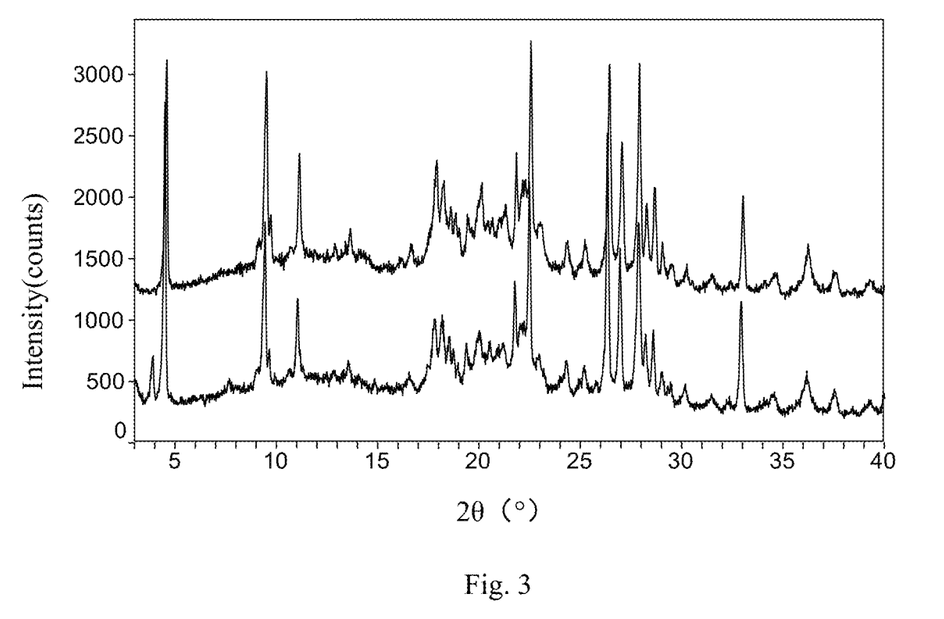
FIG. 3 is XRPD patterns of reference formulation (CN1638771A) at 0 day and 15 days under the high humidity condition (top: 0 day; bottom: 15 days).
Figure 4:
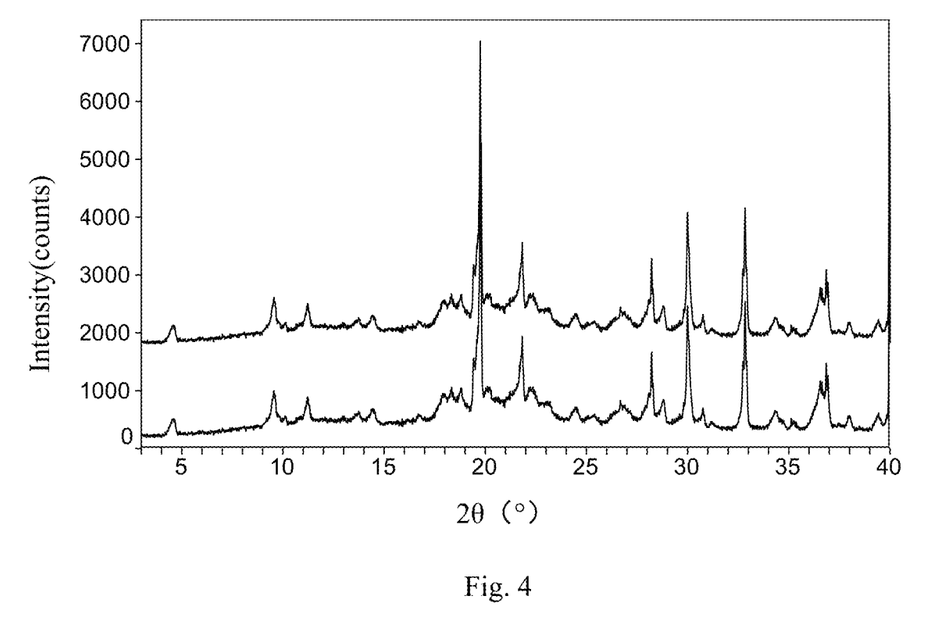
FIG. 4 is XRPD patterns of Composition 1 of the present invention at 0 day and 15 days under the high humidity condition (top: 0 day; bottom: 15 days).
Figure 5:
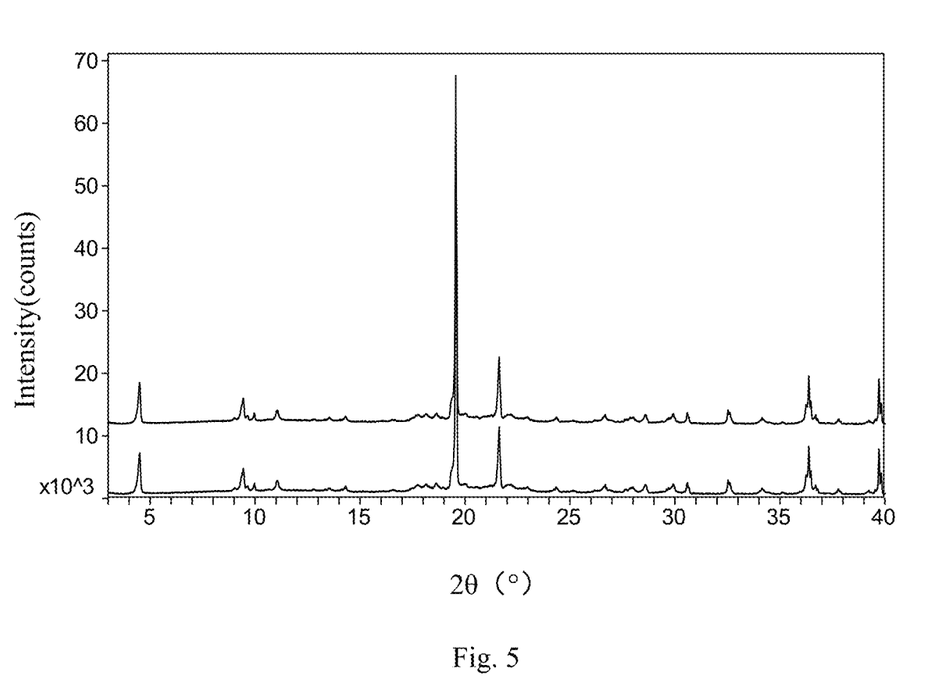
FIG. 5 is XRPD patterns of Composition 2 of the present invention at 0 day and 15 days under the high humidity condition (top: 0 day; bottom: 15 days).

A preferred embodiment of the composition is a multi-particulate formulation and the structure of the particles is shown in FIG. 2.

FIG. 2 illustrates the schematic structure of the pharmaceutical composition, a section view of a pellet suitable for the preparation of Composition 2. The approximately spherically-shaped core of this pellet contains a binder and acid substances. The core is surrendered by a first water soluble isolating layer which separates the active substance and the acid core. The isolating layer is surrounded by an active substance spherical layer which contains the binder and the active substance. The active substance spherical layer is further surrounded by a coating which serves to increase abrasion resistance and shelf life of the pellets.

The preparation method of the Composition 2 is as follows:

(1) forming the acid core of the acid substances, the disintegrant, the filler and the binder by extrusion spheronization or spheronization or fluidization;

(2) coating an acid core with the first isolating layer containing the polymer materials and drying;

(3) coating the first isolating layer with an active substance layer containing the binder and the active substance by the stacking method and drying;

(4) coating the active substance layer with the second isolating layer containing polymer materials and drying;

(5) filling the hard capsules with the obtained pellets containing the active substance.

The advantages of administration formulation prepared by Composition 2 are as follows:

1) better protecting the active substance from crystallization or degradation;

2) compared to the scheme described in the patent document CN103127109, Composition 2 has better dissolution in many dissolution media, especially in the near neutral environment such as in water, indicating a better bioavailability in people with insufficient gastric acid secretion;

3) the preparation process is simple.

EXAMPLES

The following examples are provided for further understanding the present invention, without limiting the scope of the present invention. Unless otherwise stated, the percentage is usually referred to a weight percentage.

Instruments and methods used for data collection:

X-ray powder diffraction (XRPD) was performed on a Bruker D8 Advance Diffractometer using a copper Kα X-ray with a wavelength of 1.54 nm at 40 kV and 40 mA. The instrument is configured with a θ-2θ goniometer, a Mo monochrometer and a Lynxeye detector. Before using, the instrument was performance checked using corrundum. The collection software is Diffrac Plus XRPD Commander. The sample was analyzed on a non-reflecting plate at room temperature and the details of the test conditions are as follows: 2θ scan range, 3-40°, step size, 0.02°; speed, 0.2 s/step.

High performance liquid chromatography (HPLC) data were collected using Agilent HPLC 1260 under the following conditions: column, C18 150 mm×4.6 mm; column temperature, 30° C.; wavelength, 220 nm; flow rate, 1 mL/min; injection volume, 20 μL; running time, 70 min. The solvent is 5% sodium dihydrogen phosphate buffer solution, mobile phase A is 30% of methanol and 70% of the buffer solution, mobile phase B is 60% of acetonitrile and 40% of the above buffer solution and the gradient is shown in the following table:

| Time (min) | A (%) | B (%) |
|---|---|---|
| 0 | 70 | 30 |
| 15 | 60 | 40 |
| 45 | 50 | 50 |
| 60 | 45 | 55 |
| 70 | 60 | 40 |

Unless particularly specified, the examples were all conducted at room temperature.

All reagents or raw materials used in the examples are commercially available, unless otherwise stated. The sucrose pellet core can be made in-house or obtained commercially.

Example 1

The formula of Composition 1 is shown in the following table:

| Name | Pellet core | Active substance layer | Isolating layer I | Tartaric acid | Isolating layer II | Active substance layer | Isolating layer III | ratio % | Per capsule (mg) |
|---|---|---|---|---|---|---|---|---|---|
| Sucrose pellet core | 17 | — | — | — | — | — | — | 17 | 75 |
| Dabigatran etexilate mesylate | — | 6 | — | — | — | 34 | — | 40 | 175 |
| Hemi-cysteine hydrochloride | — | — | — | 21 | — | — | — | 21 | 90 |
| Hydroxypropyl cellulose | — | 1.1 | — | 3.4 | — | 3.4 | — | 8 | 35 |
| Hydroxypropyl methyl cellulose | — | — | — | — | 1 | — | — | 2 | 7 |
| Talc | — | 1 | — | — | 1 | 3 | — | 6 | 25 |
| Gastric soluble coating layer | — | — | — | — | — | — | 7 | 7 | 30 |
| Total | | | | | | | | 100 | 437 |

Percentage composition(%) (Calculation on the basis of 150 mg of dabigatran etexilate)

The preparation procedures are as follows:

(1) preparation of the drug suspension: to 400.00 g of isopropanol, add 4.33 g of hydroxypropyl cellulose, after completely dissolving, add 110.00 g dabigatran etexilate mesylate. Add the mixtures to a IKA dispersing machine and disperses the mixture at the speed of 13000 rpm for 10 to 15 minutes, add 4.33 g of talc and continue to disperse for 10 to 15 minutes in the IKA dispersing machine. During the dispersing process, nitrogen is used to protect the mixtures and stirring is kept up during the process.

(2) applying the drug suspension: add 41.62 g of sucrose pellet cores with particle size of 200 to 355 μm into the fluidized bed, adjust the inlet temperature to 60° C. and the exhaust volume to 3 m³/min. When the product temperature reaches 30 to 40° C., adjust the atomization pressure to 1.5 Mpa and the fluidization pressure to 1.5 Mpa, begin to apply the drug suspension onto the sucrose pellet cores at the speed of about 1.5 to 2.5 g/min. After applying the drug suspension, dry it at 40 to 50° C. for 3 to 5 hours.

(3) preparation of the isolating layer I (i.e. the first isolating layer): to 60.00 g of 80% ethanol water solution, add 5.00 g of hydroxypropyl methyl cellulose, stir to dissolve completely, add the mixtures to the IKA dispersing machine for dispersion, add 3.26 g of talc gradually and disperse the mixture for 10 to 15 minutes.

(4) applying the isolating layer I: when the temperature of the material in the fluidized bed reaches 30 to 40° C., adjust the atomization pressure to 1.5 Mpa and the fluidization pressure to 1.5 Mpa, apply the isolating layer at the slurry velocity of 1.0 to 2.0 g/min, dry it at 40 to 50° C. for 3 to 7 hours after the completion of spray application.

(5) applying the acid layer: place the micro pellets obtained from the above step into a centrifugal granulator and set parameters: rotor rotation speed 350 rpm, atomization pressure 1.5 Mpa, fluid needle pressure 1.5 Mpa, inlet temperature 50° C., inlet air flow rate 1.0 m³/min, exhaust air flow rate 1.5 m³/min, slurry velocity 3.0 g/min, and powder charging speed 2.0 g/min. Add 82.23 g tartaric acid fine powder into the centrifugal granulatior and dry it at 40 to 50° C. for 5 to 6 hours.

(6) preparation of the isolating layer II (i.e. the second isolating layer): to 90.00 g of 80% ethanol water solution, add 10.00 g of hydroxypropyl methyl cellulose, stir to dissolve completely, add the mixtures to the IKA dispersing machine for dispersion, add 6.47 g of talc gradually and disperse for 10 to 15 minutes.

(7) applying the isolating layer II: when the product temperature reaches 30 to 40° C. in the fluidized bed, adjust the atomization pressure to 1.5 Mpa and the fluidization pressure to 1.5 Mpa, applying the isolating layer with the slurry velocity of 1.0 to 2.0 g/min, after the applying step is completed, dry it at 40 to 50° C. for 3 to 7 hours.

(8) preparation of the drug suspension: to 500.00 g of isopropanol solution, add 6.43 g of hydroxypropyl cellulose, after dissolve completely, add 160.00 g of dabigatran etexilate mesylate. Add the mixtures to the IKA dispersing machine and disperse at the speed of 13000 rpm for 10 to 15 minutes, add 6.33 g of talc and continue to disperse for 10 to 15 minutes in IKA dispersion machine. Nitrogen is used to protect the mixtures during the dispersing process and the stirring is kept up during the process.

(9) applying the drug suspension: charge the micro pellets obtained from the above step to the fluidized bed, adjust the inlet temperature to 60° C., exhaust volume to 3 m³/min. When the product temperature reaches 30 to 40° C., adjust the atomization pressure to 1.5 Mpa, the fluidization pressure to 1.5 Mpa and begin to apply the drug suspension at the speed of about 1.5 to 2.5 g/min. After the drug application is completed, dry it at 40 to 50° C. for 3 to 5 hours.

(10) preparation of the isolating layer III (i.e. the third isolating layer): to 160.00 g of 60% ethanol water solution, add 25.00 g of the gastric soluble coating layer, stir to dissolve completely, disperse using the IKA dispersing machine.

(11) applying the isolating layer III: when the product temperature reaches 30 to 40° C. in the fluidized bed, adjust the atomization pressure to 1.5 Mpa, the fluidization pressure to 1.5 Mpa, add the isolating layer at the slurry velocity of 1.0 to 2.0 g/min, after spray application dry the product at 40 to 50° C. for 3 to 7 hours.

(12) removing the micro pellets with the particle size over 1200 μm, filling the rest into capsules.

Example 2

The formula of the Composition 1 is shown in the following table:

| | Percentage composition (%) (Calculation on the basis of 117 mg of dabigatran etexilate) | | | | | | | Per capsule (mg) | |
|---|---|---|---|---|---|---|---|---|---|
| Name | Pellet core | Active substance layer | Isolating layer I | Tartaric acid | Isolating layer II | Active substance layer | Isolating layer III | Ratio % | |
| Sucrose pellet core | 10 | — | — | — | — | — | — | 10 | 38 |
| Dabigatran etexilate mesylate | — | 7 | — | — | — | 30 | — | 37 | 135 |
| Hemi-cysteine hydrochloride | — | — | — | 20 | — | — | — | 20 | 75 |
| Hydroxypropyl cellulose | — | 5 | — | 1 | — | 15 | — | 22 | 80 |
| Hydroxypropyl methyl cellulose | — | — | 1 | — | 1 | — | — | 2 | 6 |
| Talc | — | 1 | 1 | — | 1 | 4 | — | 6 | 24 |
| Gastric soluble coating layer | — | — | — | — | 0 | 0 | — | 2 | 9 |
| Total | | | | | | | | 100 | 367 |

The preparation procedures are the same as that of Example 1.

Example 3

The formula of the Composition 1 is shown in the following table:

| | Percentage composition (%) (Calculation on the basis of 48 mg of dabigatran etexilate) | | | | | | | Per capsule (mg) | |
|---|---|---|---|---|---|---|---|---|---|
| Name | Pellet core | Active substance layer | Isolating layer I | Tartaric acid | Isolating layer II | Active substance layer | Isolating layer III | Ratio % | |
| Sucrose pellet core | 11 | — | — | — | — | — | — | 11 | 40 |
| Dabigatran etexilate mesylate | — | 5 | — | — | — | 10 | — | 15 | 55 |
| Cysteine hydrochloride | — | — | — | 60 | — | — | — | 60 | 226 |
| Hydroxypropyl cellulose | — | 0.3 | — | 0.8 | — | 0.3 | — | 1 | 5 |
| Hydroxypropyl methyl cellulose | — | — | 1 | — | 1 | — | — | 2 | 6 |
| Talc | — | 1 | 1 | — | 1 | 1 | — | 3 | 12 |
| Gastric soluble coating layer | — | — | — | — | — | — | 9 | 9 | 34 |
| Total | | | | | | | | 100 | 378 |

The preparation procedures are the same as that of Example 1.

Example 4

The formula of the Composition 1 is shown in the following table:

| Name | Pellet core | Active substance layer | Isolating layer I | Tartaric acid | Isolating layer II | Active substance layer | Isolating layer III | Ratio % | Per capsule (mg) |
|---|---|---|---|---|---|---|---|---|---|
| | | | | Percentage composition (%) (Calculation on the basis of 190 mg of dabigatran etexilate) | | | | | |
| Sucrose pellet core | 11 | — | — | — | — | — | — | 11 | 40 |
| Dabigatran etexilate mesylate | — | 27 | — | — | — | 33 | — | 60 | 220 |
| Hemi-cysteine hydrochloride | — | — | — | 15 | — | — | — | 15 | 55 |
| Hydroxypropyl cellulose | — | 2.7 | — | 0.5 | — | 2.7 | — | 6 | 23 |
| Hydroxypropyl methyl cellulose | — | — | 1 | — | 1 | — | — | 2 | 6 |
| Talc | — | 1 | 1 | — | 1 | 1 | — | 3 | 12 |
| Gastric soluble coating layer | — | — | — | — | — | — | 3 | 3 | 12 |
| Total | | | | | | | | 100 | 368 |

The preparation procedures are the same as that of Example 1.

Example 5

The formula of the Composition 1 is shown in the following table:

| Name | Pellet core | Active substance layer | Isolating layer I | Tartaric acid | Isolating layer II | Active substance layer | Isolating layer III | Ratio % | Per capsule (mg) |
|---|---|---|---|---|---|---|---|---|---|
| | | | | Percentage composition (%) (calculation on the basis of 52 mg of dabigatran etexilate) | | | | | |
| Sucrose pellet core | 11 | — | — | — | — | — | — | 11 | 40 |
| Dabigatran etexilate mesylate | — | 8 | — | — | — | 8 | — | 16 | 60 |
| Hemi-cysteine hydrochloride | — | — | — | 38 | — | — | — | 38 | 140 |
| Hydroxypropyl cellulose | — | 2.7 | — | 14.8 | — | 2.7 | — | 20 | 75 |
| Hydroxypropyl methyl cellulose | — | — | 1 | — | 5 | — | — | 5 | 20 |
| Talc | — | 1 | 1 | — | 5 | 1 | — | 7 | 26 |
| Gastric soluble coating layer | — | — | — | — | — | — | 3 | 3 | 12 |
| Total | | | | | | | | 100 | 373 |

The preparation procedures are same to that of Example 1.

Example 6

The formula of the Composition 1 is shown in the following table:

Percentage composition (%)
(Calculation on the basis of 117 mg of dabigatran etexilate)

| Name | Pellet core | Active substance layer | Isolating layer I | Tartaric acid | Isolating layer II | Active substance layer | Isolating layer III | Ratio % | Per capsule (mg) |
|---|---|---|---|---|---|---|---|---|---|
| Sucrose pellet core | 10 | — | — | — | — | — | — | 10 | 38 |
| Dabigatran etexilate mesylate | — | 7 | — | — | — | 30 | — | 37 | 135 |
| Hemi-cysteine hydrochloride | — | — | — | 20 | — | — | — | 20 | 75 |
| Hydroxypropyl cellulose | — | 5 | — | 1 | — | 15 | — | 22 | 80 |
| Hydroxypropyl methyl cellulose | — | — | 1 | — | 1 | — | — | 2 | 6 |
| Talc | — | 1 | 1 | — | 1 | 4 | — | 6 | 24 |
| Gastric soluble coating layer | — | — | — | — | 0 | 0 | — | 2 | 9 |
| Total | | | | | | | | 100 | 367 |

The preparation procedures are the same as that of Example 1.

Example 7

The formula of the Composition 2 is shown in the following table:

Percentage composition (%)
(Calculation on the basis of 150 mg of dabigatran etexilate)

| Name | acid pellet core | Isolating layer I | Active substance layer | Isolating layer II | Ratio % | Per capsule (mg) |
|---|---|---|---|---|---|---|
| Sucrose | 10 | — | — | — | 10 | 40 |
| Hcysteine hydrochloride | 29 | — | — | — | 29 | 120 |
| Dabigatran etexilate mesylate | — | — | 41 | — | 41 | 173 |
| Hydroxypropyl cellulose | 4 | 1 | 7 | — | 12 | 50.86 |
| Hydroxypropyl methyl cellulose | — | — | — | — | | 0 |
| Talc | — | 1 | 4 | — | 5 | 20.87 |
| Gastric soluble coating layer | — | — | — | 4 | 4 | 16.26 |
| Total | | | | | 100 | 420.99 |

The preparation procedures are shown below:

(1) preparation of the acid pellet core: mixing 37.57 g of sucrose and 250.00 g of hemi-cysteine hydrochloride homogeneously, place the mixture into an extrusion spheronization machine, set the rotor rotation speed at 150 rpm and the screen mesh 600 μm, turn on the machine, add 5% hydroxypropyl cellulose solution, obtain extruded particles, place the particles into the centrifugal granulatior, spheronization at a speed of 400 rpm and dry the spheronized particles at 40 to 50° C. for 5 to 8 hours.

(2) preparation of isolating layer I (i.e. the first isolating layer): to 90.00 g of 80% ethanol water solution, add 12.00 g of hydroxypropyl methyl cellulose, stir to dissolve completely, add the mixtures to a IKA dispersing machine for dispersion, add 7.48 g of talc gradually and disperse for 10 to 15 minutes.

(3) applying isolating layer I: when the product temperature reaches 30 to 40° C. in the fluidized bed, adjust the atomization pressure to 1.5 Mpa and the fluidization pressure to 1.5 Mpa, apply the isolating layer with the slurry velocity of 1.0 to 2.0 g/min, after the spray application dry the material at 40 to 50° C. for 3 to 7 hours.

(4) preparation of the drug suspension: to 900.00 g of isopropanol solution, add 8.33 g of hydroxypropyl cellulose, after dissolve completely, add 250.00 g of dabigatran etexilate mesylate. Add the mixtures to the IKA dispersing machine and disperse at the speed of 13000 rpm for 10 to 15 minutes. Add 8.33 g of talc and continue to disperse for 10 to 15 minutes in the IKA dispersing machine. Nitrogen is used to protect the mixtures and the stirring is kept up during the dispersing process.

(5) applying the active substance layer: place the micro pellets obtained from the above step into a centrifugal granulatior and set the parameters: rotor rotation speed 350 rpm, atomization pressure 1.5 Mpa, fluid needle pressure 1.5 Mpa, inlet temperature 50° C., inlet air flow rate 1.0 m³/min, exhaust air flow rate 1.5 m³/min, slurry velocity 3.0 g/min, powder charging speed 2.0 g/min. Add 749.96 g of tartaric acid fine powders into the centrifugal granulator, dry the material at 40 to 50° C. for 5 to 6 hours.

(6) preparation of the isolating layer II (i.e. the second isolating layer): to 160.00 g of 60% ethanol water solution, add 25.00 g of the gastric soluble coating layer, stir to dissolve completely, add the mixtures to the IKA dispersing machine for dispersion.

(7) applying isolating layer II: when the product temperature reaches 30 to 40° C. in the fluidized bed, adjust atomization pressure to 1.5 Mpa and fluidization pressure to 1.5 Mpa, apply the isolating layer with the slurry velocity of 1.0 to 2.0 g/min, after the spraying process, dry the product at 40 to 50° C. for 3 to 7 hours.

(8) removing the micro pellets with particle size over 1200 μm, filling the rest into capsules.

Example 8

The formula of the Composition 2 is shown in the following table:

| Name | Acid pellet core | Iso-lating layer I | Active substance layer | Iso-lating layer II | Ratio % | Per capsule (mg) |
|---|---|---|---|---|---|---|
| Percentage composition (%) (Calculation on the basis of 24 mg of dabigatran etexilate) | | | | | | |
| Sucrose | 11 | — | — | — | 11 | 30 |
| Hemi-cysteine hydrochloride | 65 | — | — | — | 65 | 175 |
| Dabigatran etexilate mesylate | — | — | 10 | — | 10 | 28 |
| Hydroxypropyl cellulose | 0.5 | — | 1.9 | — | 3 | 9.4 |
| Hydroxypropyl methyl cellulose | — | 1 | — | — | | 0 |
| Talc | — | 1 | 6 | — | 8 | 20.3 |
| Gastric soluble coating layer | — | — | — | 2 | 2 | 6 |
| Total | | | | | 100 | 268.7 |

The preparation procedures are the same as that of Example 7.

Example 9

The formula of the composition 2 is shown in the following table:

| Name | Acid pellet core | Iso-lating layer I | Active substance layer | Iso-lating layer II | Ratio % | Per capsule (mg) |
|---|---|---|---|---|---|---|
| Percentage composition (%) (Calculation on the basis of 24 mg of dabigatran etexilate) | | | | | | |
| Sucrose | 20 | — | — | — | 20 | 30 |
| Hcysteine hydrochloride | 10 | — | — | — | 10 | 15 |
| Dabigatran etexilate mesylate | — | — | 18 | — | 18 | 28 |
| Hydroxypropyl cellulose | 17.1 | — | 3.3 | — | 20 | 31 |
| Hydroxypropyl methyl cellulose | — | 5 | — | — | 5 | 8 |
| Talc | — | 5 | 11 | — | 17 | 25.3 |
| Gastric soluble coating layer | — | — | — | 10 | 10 | 15 |
| Total | | | | | 100 | 152.3 |

The preparation procedures are same to that of Example 7.

Example 10

The formula of the Composition 2 is shown in the following table:

| Name | Acid pellet core | Iso-lating layer I | Active substance layer | Iso-lating layer II | Ratio % | Per capsule (mg) |
|---|---|---|---|---|---|---|
| Percentage composition (%) (Calculation on the basis of 173 mg of dabigatran etexilate) | | | | | | |
| Sucrose | 8 | — | — | — | 8 | 25 |
| Hemi-cysteine hydrochloride | 8 | — | — | — | 8 | 25 |
| Abigatran etexilate methyl sulfonate | — | — | 65 | — | 65 | 200 |
| Hydroxypropyl cellulose | 1.6 | — | 1.6 | — | 3 | 10 |
| Hydroxypropyl methyl cellulose | — | 3 | — | — | 3 | 8 |
| Talc | — | 3 | 6 | — | 8 | 25.3 |
| Gastric soluble coating layer | — | — | — | 5 | 5 | 15 |
| Total | | | | | 100 | 308.3 |

The preparation procedures are the same as that of Example 7.

Comparative Example 1

Composition 1 prepared by the present invention, Composition 2 prepared by the present invention and the commercially available reference formulation (CN1638771A) were placed under high humidity for 15 days and the results are compared and shown in Table 1.

The experimental methods are as follows: take 5 g each of encapsulated materials from Composition 1 prepared by the present invention, Composition 2 prepared by the present invention and the commercially available reference formulation (CN1638771A), place them on the petri dish and place them under the condition of RH92.5%. After 15 days, test the samples using XRPD to characterize the phase transformation of the active substance. Take 100 mg each of encapsulated material, dilute 250 times and analyze the samples using high performance liquid chromatography. The results are shown in Table 1.

TABLE 1

Comparative results from 0 day and 15 days under the high humidity condition

| Composition | Time (day) | Appearance | Form | Related substances (%) Total | Maximum individual impurity | Assay (%) |
|---|---|---|---|---|---|---|
| Reference formulation | 0 | Yellow particles | — | 0.44% | 0.08% | 99.56% |
|  | 15 | Yellow particles with sticky surface | Different from the pattern of 0 day | 1.74% | 0.15% | 98.26% |
| Composition 1 prepared by the present invention | 0 | Off-white particles | — | 0.59% | 0.09% | 99.32% |
|  | 15 | Off-white particles | Same as the pattern of 0 day | 0.74% | 0.12% | 99.24% |
| Composition 2 prepared by the present invention | 0 | Off-white particles | — | 0.57% | 0.10% | 99.33% |
|  | 15 | Off-white particles | Same as the pattern of 0 day | 0.79% | 0.12% | 99.09% |

The results in Table 1 indicate that two compositions prepared by the present invention have no phase transformation under the high humidity condition for 15 days and there is a small change in related substances and assay value. However, the crystalline form of the active substance from the commercially available reference formulation (CN1638771A) has changed (an unknown diffraction peak appears at about 3.8 2θ angle) after 15 days. In addition, there is a big change in related substance and assay value. The results indicate that the chemical stability and physical stability of the two pharmaceutical compositions prepared by the present invention are better than that of the commercially available reference formulation (CN1638771A).

Comparative Example 2

Dissolution tests in water of Composition 1 prepared by the present invention, Composition 2 prepared by the present invention, commercially available reference formulation (CN1638771A) and the composition prepared according to the example 30 of the patent document CN103127109A (Reference 2) were conducted, and the results are shown in Table 2.

The experimental methods are as follows: take three capsules each from Composition 1 prepared by the present invention, Composition 2 prepared by the present invention, the commercially available reference formulation and Reference 2, and test at the condition of 100 rpm, using the basket method and 900 mL water as the dissolution medium. Sample 10 ml solution at 5 minutes, 10 minutes, 15 minutes, 20 minutes and 30 minutes of the dissolution test, filter and analyze the filtrate using high performance liquid chromatography. The results are shown in Table 2.

TABLE 2

Comparison of the dissolution in Water

| Time (min) | Percent Dissolved (%) | | | |
|---|---|---|---|---|
|  | Composition 1 | Composition 2 | Reference formulation | Reference 2 |
| 0 | 0 | 0 | 0 | 0 |
| 5 | 1.1 | 2.4 | 3.4 | 1.1 |
| 10 | 76.7 | 74.4 | 60.4 | 49.7 |
| 15 | 95.1 | 94.4 | 90.1 | 55.7 |
| 25 | 94.4 | 95.1 | 92.6 | 60 |

Note: in Table 2, the "time" refers to the dissolution time after subtracting the time needed for the capsule shells to dissolve.

According to the guidance for in vitro dissolution profile comparison for product sameness, when two formulations are more than 85% dissolved within 15 minutes, the two formulations are similar in vitro dissolution behaviors. The results of Table 2 indicate that the dissolution of Composition 1 and Composition 2 is similar to that of the reference formulation in water, however, the dissolution of Reference 2 does not meet the criteria at all. Those results indicate that in vitro dissolution behaviors of the product of Composition 1 and Composition 2 of the present invention are similar to that of reference formulation, and a better bioavailability for Compositions 1 and 2 of the present invention than Reference 2 in human with insufficient gastric acid secretion.

The above description is just specific embodiments of the present invention and the scope of the invention should not be limited by the embodiments. Various changes or replacements of the embodiments without any creative work should be within the scope of the present invention to those skilled in the art.

What is claimed is:
1. A pharmaceutical composition for oral administration comprising:
  a) a spherically-shaped pellet core comprising:
    10-17 wt. % sucrose by weight of the composition;
  b) a first active substance layer surrounding the spherically-shaped pellet core, wherein the first active substance layer comprises:

6-65 wt. % dabigatran etexilate, or a pharmaceutically acceptable salt thereof, by weight of the composition,
1.1-15 wt. % hydroxypropyl cellulose binder by weight of the composition, and
1-4 wt. % talc by weight of the composition;
c) optionally, a first isolating layer surrounding the first active substance layer, wherein the optional first isolating layer comprises:
1-5 wt. % hydroxypropyl methyl cellulose binder by weight of the composition, and
1-5 wt. % talc by weight of the composition;
d) an acid layer surrounding the first active substance layer or the optional first isolating layer when present, wherein the acid layer comprises:
20-60 wt. % hemi-cysteine hydrochloride organic acid by weight of the composition, and
1-14.8 wt. % hydroxypropyl cellulose binder by weight of the composition,
e) a second isolating layer surrounding the acid layer, wherein the second isolating layer comprises:
1-5 wt. % hydroxypropyl methyl cellulose binder by weight of the composition, and
1-5 wt. % talc by weight of the composition;
f) a second active substance layer surrounding the second isolating layer, wherein the second active substance layer comprises:
6-65 wt. % dabigatran etexilate, or a pharmaceutically acceptable salt thereof, by weight of the composition,
1.1-15 wt. % hydroxypropyl cellulose binder by weight of the composition, and
1-4 wt. % talc by weight of the composition; and
g) optionally a third isolating layer surrounding the second active substance layer, wherein the optional third isolating layer comprises 3-9 wt. % of a gastric soluble coating selected from the group consisting of hydroxypropyl methyl cellulose, hydroxypropyl cellulose, starch, and combination thereof.

2. The pharmaceutical composition according to claim 1, wherein the pharmaceutical composition comprises c) the first isolating layer.

3. The pharmaceutical composition according to claim 1, wherein the pharmaceutical composition comprises g) the third isolating layer.

4. The pharmaceutical composition according to claim 3, wherein the gastric soluble coating is hydroxypropyl methyl cellulose.

5. The pharmaceutical composition according to claim 3, wherein the gastric soluble coating is hydroxypropyl cellulose.

6. The pharmaceutical composition according to claim 3, wherein the gastric soluble coating is starch.

7. The pharmaceutical composition according to claim 1, wherein the pharmaceutical composition is more than 85% dissolved within 15 minutes, when tested at the condition of 100 rpm, using the basket method and 900 mL water as the dissolution medium.

8. The pharmaceutical composition according to claim 7, wherein the pharmaceutical composition is about 95.1% dissolved within 15 minutes, when tested at the condition of 100 rpm, using the basket method and 900 mL water as the dissolution medium.

9. A pharmaceutical composition for oral administration comprising:
a) a spherically-shaped pellet core comprising:
10-17 wt. % sucrose by weight of the composition;
b) a first active substance layer surrounding the spherically-shaped pellet core, wherein the first active substance layer comprises:
6-65 wt. % dabigatran etexilate, or a pharmaceutically acceptable salt thereof, by weight of the composition,
1.1-15 wt. % hydroxypropyl cellulose binder by weight of the composition, and
1-4 wt. % talc by weight of the composition;
c) a first isolating layer surrounding the first active substance layer, wherein the first isolating layer comprises:
1-5 wt. % hydroxypropyl methyl cellulose binder by weight of the composition, and
1-5 wt. % talc by weight of the composition;
d) an acid layer surrounding the first isolating layer, wherein the acid layer comprises:
20-60 wt. % hemi-cysteine hydrochloride organic acid by weight of the composition, and
1-14.8 wt. % hydroxypropyl cellulose binder by weight of the composition,
e) a second isolating layer surrounding the acid layer, wherein the second isolating layer comprises:
1-5 wt. % hydroxypropyl methyl cellulose binder by weight of the composition, and
1-5 wt. % talc by weight of the composition;
f) a second active substance layer surrounding the second isolating layer, wherein the second active substance layer comprises:
6-65 wt. % dabigatran etexilate, or a pharmaceutically acceptable salt thereof, by weight of the composition,
1.1-15 wt. % hydroxypropyl cellulose binder by weight of the composition, and
1-4 wt. % talc by weight of the composition; and
g) optionally a third isolating layer surrounding the second active substance layer, wherein the optional third isolating layer comprises 3-9 wt. % of a gastric soluble coating selected from the group consisting of hydroxypropyl methyl cellulose, hydroxypropyl cellulose, starch, and combination thereof.

10. The pharmaceutical composition according to claim 9, wherein the pharmaceutical composition comprises g) the third isolating layer.

11. The pharmaceutical composition according to claim 9, wherein the pharmaceutical composition is more than 85% dissolved within 15 minutes, when tested at the condition of 100 rpm, using the basket method and 900 mL water as the dissolution medium.

12. The pharmaceutical composition according to claim 11, wherein the pharmaceutical composition is about 95.1% dissolved within 15 minutes, when tested at the condition of 100 rpm, using the basket method and 900 mL water as the dissolution medium.

13. A pharmaceutical composition for oral administration comprising:
a) a spherically-shaped pellet core comprises:
10-17 wt. % sucrose by weight of the composition;
b) a first active substance layer surrounding the spherically-shaped pellet core, wherein the first active substance layer comprises:
6-65 wt. % dabigatran etexilate, or a pharmaceutically acceptable salt thereof, by weight of the composition,
1.1-15 wt. % hydroxypropyl cellulose binder by weight of the composition, and
1-4 wt. % talc by weight of the composition;

c) an acid layer surrounding the first active substance layer, wherein the acid layer comprises:
   20-60 wt. % hemi-cysteine hydrochloride organic acid by weight of the composition, and
   1-14.8 wt. % hydroxypropyl cellulose binder by weight of the composition,
d) an isolating layer surrounding the acid layer, wherein the isolating layer comprises:
   1-5 wt. % hydroxypropyl methyl cellulose binder by weight of the composition, and
   1-5 wt. % talc by weight of the composition;
e) a second active substance layer surrounding the isolating layer, wherein the second active substance layer comprises:
   6-65 wt. % dabigatran etexilate, or a pharmaceutically acceptable salt thereof, by weight of the composition,
   1.1-15 wt. % hydroxypropyl cellulose binder by weight of the composition, and
   1-4 wt. % talc by weight of the composition; and
f) a further optional isolating layer surrounding the second active substance layer, wherein the further optional isolating layer comprises 3-9 wt. % of a gastric soluble coating selected from the group consisting of hydroxypropyl methyl cellulose, hydroxypropyl cellulose, starch, and combination thereof.

14. The pharmaceutical composition according to claim 13, wherein the pharmaceutical composition comprises the f) further optional isolating layer.

15. The pharmaceutical composition according to claim 14, wherein the pharmaceutical composition is more than 85% dissolved within 15 minutes, when tested at the condition of 100 rpm, using the basket method and 900 mL water as the dissolution medium.

16. The pharmaceutical composition according to claim 15, wherein the pharmaceutical composition is about 95.1% dissolved within 15 minutes, when tested at the condition of 100 rpm, using the basket method and 900 mL water as the dissolution medium.

* * * * *